United States Patent [19]

Whitehead

[11] Patent Number: 5,004,894
[45] Date of Patent: Apr. 2, 1991

[54] CLOTH WARMER

[76] Inventor: Jimmy Whitehead, 5500 Brookhaven, Mobile, Ala. 36693

[21] Appl. No.: 252,783

[22] Filed: Oct. 3, 1988

[51] Int. Cl.$^5$ .............................................. H05B 3/10
[52] U.S. Cl. ..................................... 219/521; 219/386
[58] Field of Search ............... 219/521, 385, 386, 387, 219/535, 429, 430, 432, 433, 439

[56] References Cited

U.S. PATENT DOCUMENTS

| 2,417,802 | 3/1947 | Longstreet | 219/433 |
| 2,520,543 | 8/1950 | Hawkins | 219/386 |
| 2,627,017 | 1/1953 | Howard | 219/521 |
| 4,191,524 | 3/1980 | Thorn | 219/521 |
| 4,215,843 | 8/1980 | Gay | 219/521 |
| 4,419,568 | 12/1983 | VanOverloop | 219/521 |
| 4,675,506 | 6/1987 | Nusbaum | 219/411 |
| 4,694,973 | 9/1987 | Rose | 219/521 |

FOREIGN PATENT DOCUMENTS 242272  9/1946  Switzerland ........................ 219/429

Primary Examiner—Teresa J. Walberg
Attorney, Agent, or Firm—Gregory M. Friedlander

[57] ABSTRACT

A heating chamber having a compartment which provides for heat sensitive packages of paper or cloth moistened cleaning wipes to be held for warming. The invention incorporates a heat deflector to assure that the heat is not directed against the bottom of the chamber. Heat conducting spaces insulated by outerwalls assure the container is evenly heated. There is easy access to and replacement of the package held. In the preferred embodiment, the container is held above the chamber floor and heat deflector so as to prevent direct heat from damaging the bottom of the container.

15 Claims, 3 Drawing Sheets

CLOTH WARMER

BACKGROUND OF INVENTION

1. Field of Invention

The present invention relates to warming chambers.

More particularly the invention relates to warming chambers for warming moistened paper or cloth wipes in a heat sensitive package, such as thin plastic, in which such wipes come from suppliers.

2. Discussion of Prior Art

The present invention is specifically directed to the use of warming moistened paper or cloth wipes, referred to herein generally as cloth wipes. A warm temperature may be desired for comfort, but not for other reasons. Cloth wipes have a variety of uses. Recently, cloth wipes for cleansing very young children have become popular due to the ease with which these may be provided in inexpensive disposable plastic containers.

When used, especially at winter room temperature, the cloth wipes are extremely uncomfortable due to evaporation cooling the surface of the wipe below room temperature. This discomfort is communicated by having the child upset.

The present device is directed towards reducing this problem by providing a means for maintaining a warm environment for the disposable cloth wipe container so as to keep the moistened cloth wipes at a desired temperature.

The concept of using a light bulb as a heating device is an old technique for generating heat, as is the use of the light bulb to generate a night light. The prior art covering this does not regulate the heat or hold the container in such a way as to prevent drying and heat damage. The items to be warmed and dried sit on the chamber bottom usually in direct contact with a heated plate.

A peanut heater has been shown having a hinged, transparent, access cover and a flange for holding a container and the container which is held apart from the sides of a heated chamber without a heat deflector.

In the prior art of heating using a chambered light bulb, it is a desired result to maintain a certain temperature for a certain use. Overheating is generally not a problem addressed and, hence, heat deflectors are not shown. The designs are not made for holding disposable heat sensitive containers.

Devices for holding warmed towels in the prior art require special bulbs or do not heat the entire container. Additionally, there is no provision in the prior warmed towel dispensers for a heat deflector and means to prevent the fluid, in the event of a leak, from causing a potential electric fire.

The invention disclosed herein also allows for inserts to be designed and made so that a container of any shape can be used within the volume limitations of the insert holder without expensive retooling.

It is, therefore, an object of this invention to provide a warmer for moistened cloth wipes.

It is a further object of this invention to provide a warmer which will easily hold and discharge containers for moistened cloth wipes.

It is a further object of this invention to provide a warmer which will not damage the heat sensitive containers which are used to package moistened cloth wipes.

It is a further object of this invention to provide a warmer which is designed to hold a variety of different cloth wipe containers.

These and other objects and advantages of the invention will become better understood hereinafter from a consideration of the specification with reference to the accompanying drawings forming part thereof, and in which like numerals correspond to parts throughout the several views of the invention.

BRIEF DESCRIPTION of the DRAWINGS

For a further understanding of the nature and objects of the present invention, reference should be had to the following detailed description taken in conjunction with the accompanying drawings in which like parts are given like reference numerals and wherein.

DETAILED DESCRIPTION of the PREFERRED EXEMPLARY EMBODIMENT(S)

Figure 1:
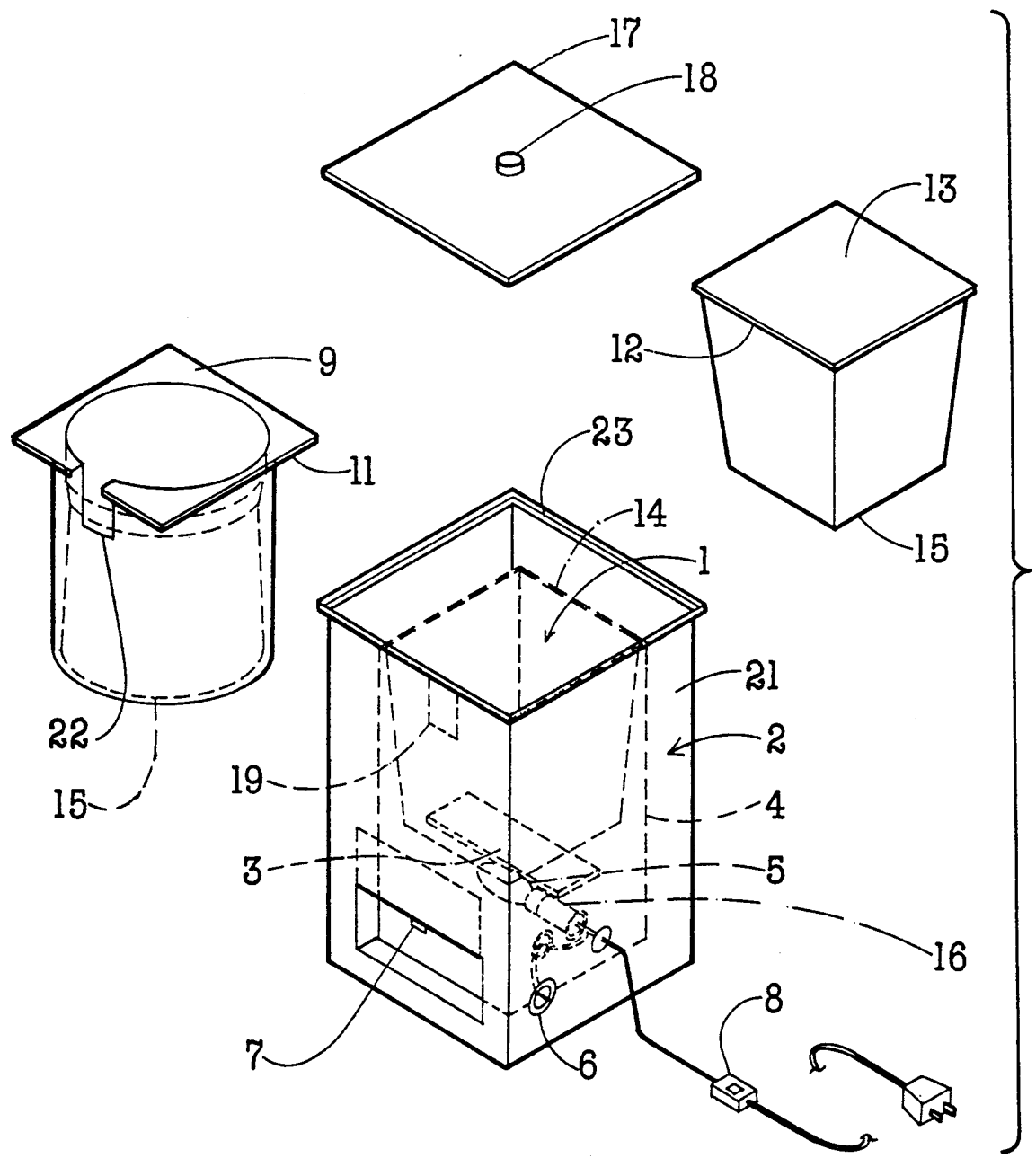
FIG. 1 is a perspective view of the invention showing the accessories and warmed packages removed.

As can best be seen by reference to FIG. 1 the invention has an inner chamber 1 defined by two to four inner walls 4 with a ridge 14 along the top of the inner walls 4 for receiving the lip 12 of container 15. Container 15 is a standardized container for holding moistened cloth wipes. Inner chamber 1 lies within outer insulating chamber 2 defined by four outer walls 21.

At the bottom of chamber 1 is a warming means or heat source 5, in the preferred embodiment, a light bulb 5. Light bulb 5 is energized by socket 16 which is, in turn, controlled by rheostat 6 and on/off switch 8. Between heat source 5 and the top portion of chamber 1 there is a heat deflector 3.

In the preferred embodiment, when in use, the container 15 is lowered into the inner chamber 1. This distance between ridge 14 and heat deflector 3 is sufficient so that when fully lowered, lip 12 rests on ridge 14 and the bottom of container 15 is held above and out of contact with heat deflector 3. Heat deflector 3 is smaller in area than chamber 1 so that heated air freely circulates between the top and bottom of chamber 1 around container 15.

Figures 2, 3:
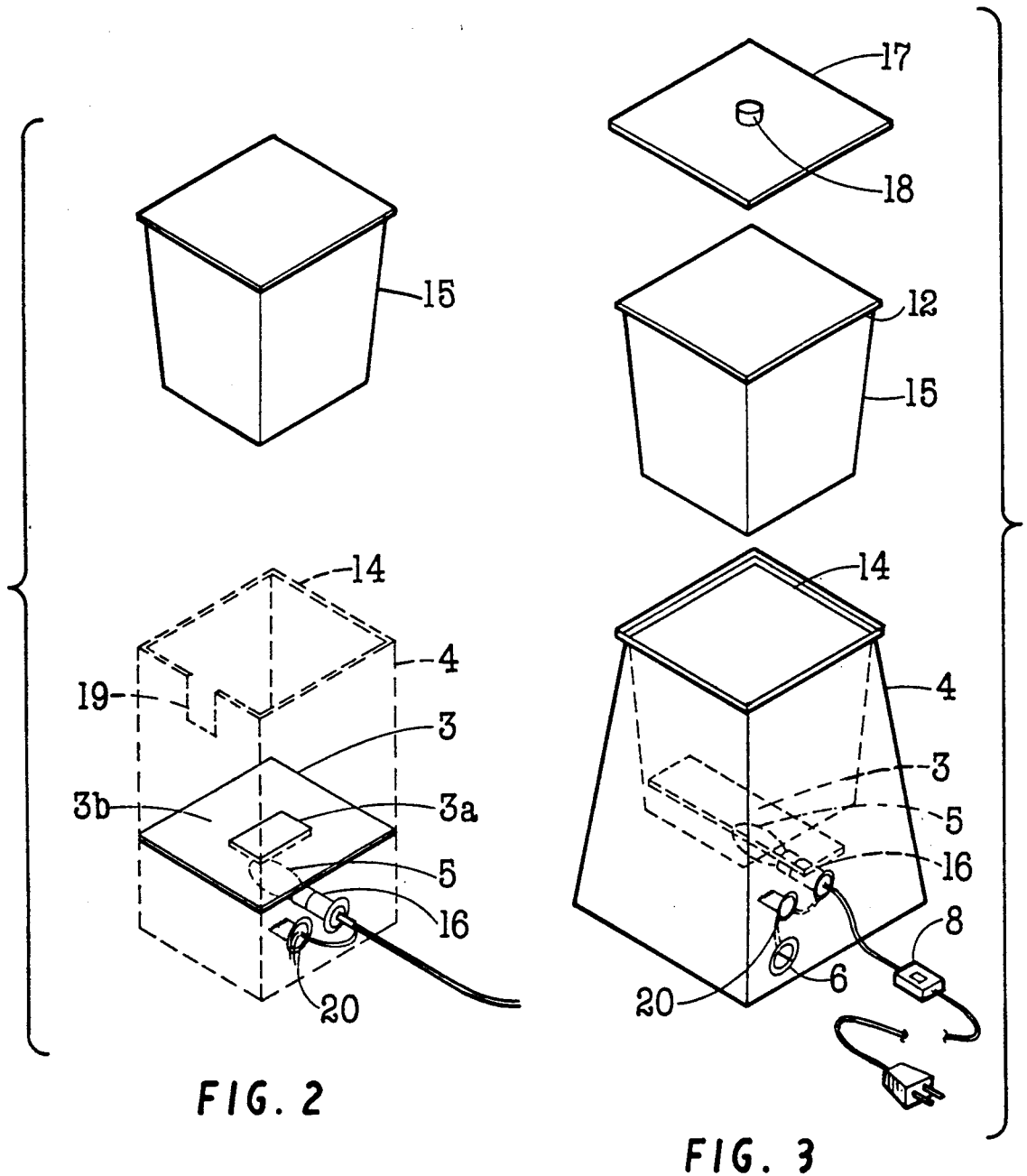
FIG. 2 shows a modified heat deflector providing a seal between the warming element and warming chamber.
FIG. 3 shows an alternate embodiment having a single chamber allowing for air circulation
Figure 4:
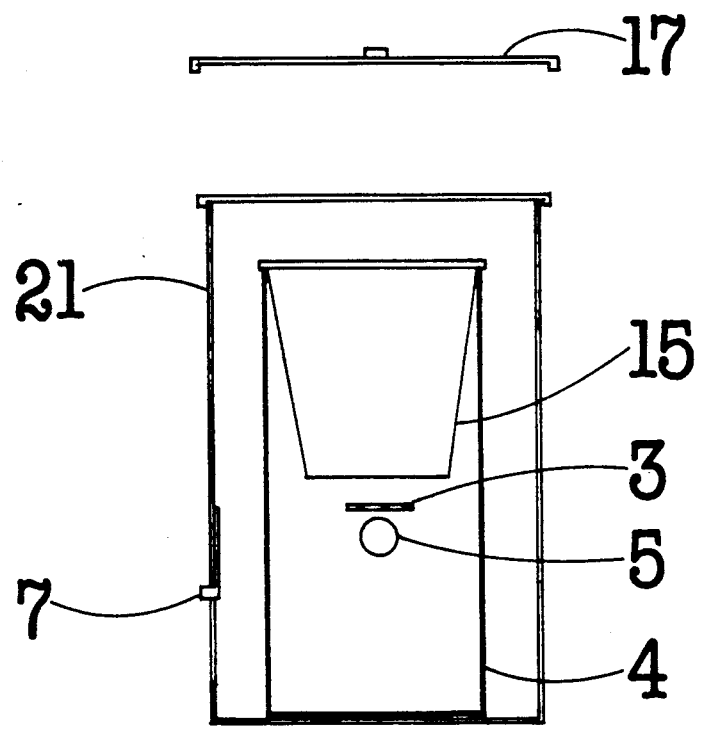
FIG. 4 shows a sectional view of the embodiment shown in FIG. 1 along the vertical axis A—A.

As shown in FIG. 2, deflector 3 may be a solid shield or floor 3 dividing chamber 1 or may define perforations to allow for air to circulate.

Light bulb 5 is elevated above the bottom of inner chamber 1 and outer chamber 2 so that if liquid leaks, it will accumulate below the heat source 5 to prevent shock and fire. A solid heat shield 3 would prevent any fluid from reaching the heat source 5, but any shield could be curved to channel the flow of any leaks away from the heat source 5. In the preferred embodiment, heat deflector 3 is attached to wall 4 above socket 16 and extends over light bulb 5.

As shown in FIG. 2, heat deflector 3 may have a heat resistant on non-conducting center 3(a) surrounding an otherwise solid, heat permeable base 3(b). This may be accomplished by having a greater thickness to the center of heat deflector 3(a) than the surrounding base 3(b) or by having a strip of more heat resistant material at the center 3(a). This embodiment would prevent fluid from the container 15 from leaking into the bottom half of the chamber 1 and allow for container 15 to be in direct contact with heat resistant center 3(a).

Heat deflector 3 is made of Lexan TM or a similar heat resistant and reflective material so that direct heat is deflected away from the bottom of container 15. The area of heat deflector 3 is at least as wide as light bulb 5.

Outer chamber 2 is of translucent or transparent material so that light from the container illuminates the room. This night light function is provided so no additional lighting, which might further disturb the child, is added when entering the room where the device is kept. The amount of light is regulated by having different amounts of opacity or paint on the outer chamber walls 21.

In the preferred embodiment, the inner chamber 1 fits within an outer chamber 2. This outer chamber 2 is heat insulating so as to keep the inner chamber 1 at a desired temperature. An air space may be defined by the distance between the walls 21 of outer chamber 2 and the walls 4 of inner chamber 1. The walls 21 of outer Chamber 2 may be opaque. A door 7 may be provided in one or more walls 21 of outer chamber 2 as shown in FIG. 1. This door 7 when opened provides additional light. This light may be shut off when the door 7 is closed.

Most containers 15 have a removable lid 13. The device has an additional cover 17 which may be put in place and in contact with outer chamber 2. Cover 17 has a handle 18 which does not conduct heat to allow it to be easily removed or lifted.

In the preferred embodiment, cover 17 may be used regardless of whether or not lid 13 is in place. The top of the walls of outer chamber 2 are slightly raised above the ridge 14 of inner chamber 1 so that cover 17 fits onto outer chamber 2 without interfering with the lid 13. The walls 21 define a recess 23 within which cover 17 fits to better insulate the inner chamber 1. Cover 17 may fit at a height above lid 13 to allow better heat circulation, but in the preferred embodiment, cover 17 fits directly over lid 13 to hold lid 13 in place to help prevent drying and to replace lid 13 if lid 13 comes loose or is lost.

FIG. 3 shows an alternate embodiment of the device having only a single chamber 1. In FIG. 3, a truncated square pyramid shaped inner chamber 1 is formed by having the four walls meet to form the ridge 14. The walls may then curve outward or upward to receive the removable cover 17. Since the disposable container 15 has a constant base area, the pyramidal shape provides allows free air circulation due to its expanding volume from the top down. Heat deflector 3 serves the same purpose in this embodiment.

Since containers 15 may be of various sizes shapes, an adapter 9 shown in FIG. 1 is envisioned. Adapter 9 is specifically adapted to round containers, but may be of any size and shape.

The purpose of adapter 9 is to hold a different sized container 15. To accomplish this, adapter 9 has a projection 11 which is designed to fit along ridge 14 in place of plastic lip 12. Similarly, adapter 9 may replace inner chamber 1 entirely although in the preferred embodiment, which is specially designed for square containers 15, this is not necessary. Adapter 9 may be water proof to prevent leakage or have openings to allow circulation with air without adapter 9. However, regardless of its other features, it allows for heat to circulate or pass through the walls of adapter 9 to the walls of container 15, so that the inner container 15 is warmed.

Adapter 9 is made of suitable material and design so that, when in place, it does not overly interfere with the flow of heat within chamber 1 or the placement of lid 17.

Ridge 14 of inner chamber 1 has one or more notches 19 to allow for easy removal of container 15. Notch 19 is a space defined in the upper wall of chamber 1 and ridge 14 which allows for the user to insert a finger to lift the plastic container 15 without undue interference from the otherwise completely encircling outer ridge 14. The adapter 9 has at least one slot 22 for the same purpose as notch 19. The notch 19 may be at the top of chamber 1 or may travel the entire length of the chamber 1. Similarly the slot 22 may be only along the top of the adapter wall with adapter 9 or may travel the length of the adapter wall. The slot 22 is preferably of less width than notch 19 so that the edge of slot 22 may be reached even when slot 22 and notch 19 are aligned.

Because many varying and different embodiments may be made within the scope of the inventive concept herein taught and because many modifications may be made in the embodiment(s) herein detailed in accordance with the descriptive requirements of the law, it is to be understood that the details herein are to be interpreted as illustrative and not in a limiting sense.

What is claimed is:

1. A cloth warmer warming moistened cloth towels in a container having a lip and lid comprising:
    (a) at least 2 inner walls and a floor defining an inner chamber defining a ridge along an upper most edge of the inner walls for receiving the lip wherein at least one of said inner walls defines a notch;
    (b) an outer chamber made of insulating material:
    (c) a warming means within a lower portion of the inner chamber and fixedly attached to the inner chamber;
    (d) a heat deflector means disposed above the warming means and below the ridges, said heat deflector means being attached to the inner chamber above a point of attachment of the warming means.

2. A cloth warmer warming moistened cloth towels in a container having a lip and lid comprising:
    (a) at least 2 inner walls and a floor defining an inner chamber defining a ridge along an upper most edge of the inner walls for receiving the lip;
    (b) an outer chamber made of insulating material:
    (c) a warming means within a lower portion of the inner chamber and fixedly attached to the inner chamber;
    (d) a heat deflector means disposed above the warming means and below the ridges, said heat deflector means being attached to the inner chamber above a point of attachment of the warming means.

3. The cloth warmer of claim 2 wherein the heat deflector means comprises a strip of heat resistant material fixed to the side of said chamber between the warming means and the ridge at such a distance from the ridge that the container is held above the deflector when the lip of the container is in contact with the ridge.

4. The cloth warmer of claim 2 wherein the outer chamber is higher than the inner walls by a height equal to the distance between the top of the container and bottom of the container lip and further comprising:
    (a) a cover for said outer chamber.

5. The cloth warmer of claim 4 wherein the outer walls form a recess to receive the cover.

6. The cloth warmer of claim 2 wherein the warming means comprises of a light bulb.

7. The cloth warmer of claim 6 wherein the light bulb fits through an inner wall and wherein the heat deflector is attached to the same wall directly over the bulb having a width at least equal to the width of the light bulb and being at least as long as the light bulb.

8. A cloth warmer warming moistened cloth towels in a container having a lip and lid comprising:
   (a) at least 2 inner walls and a floor defining an inner chamber defining a ridge along an upper most edge of the inner walls for receiving the lip;
   (b) an outer chamber made of insulating material;
   (c) a warming means within a lower portion of the inner chamber and fixedly attached to the inner chamber;
   (d) a heat deflector means disposed above the warming means and below the ridges, said heat deflector means being attached to the inner chamber above a point of attachment of the warming means;
   (e) an adapter having an adapter wall and an adapter floor of sufficient volume to allow a smaller container to fit within the adapter, said adapter having a projection for contact against the ridge, the projection fitting loosely against the ridge along the circumference of the ridge.

9. The cloth warmer of claim 8 wherein the adapter wall of said adapter defines a slot.

10. The cloth warmer of claim 9 wherein the adapter slot is of lesser width than the notch.

11. A cloth warmer warming moistened cloth towels in a container comprising;
   (a) an insulating outer walls chamber having at least three outer walls defining a recess;
   (b) a heating means within said insulating walls and anchored to one of the walls;
   (c) an adapter with sufficient volume to hold a container having a projection along the adapter of like shape to the recess to fit within and contact the recess.

12. A cloth warmer warming moistened cloth towels in a container comprising;
   (a) an insulating outer walls chamber having at least three outer walls defining a recess;
   (b) a heating means within said insulating walls and anchored to one of the walls;
   (c) an adapter with sufficient volume to hold a container having a projection along the adapter of like shape to the recess to fit within and contact the recess;
   (d) a heat deflector attached to the outer wall above said heating means and below the adapter when the projection is in contact with the recess.

13. A cloth warmer warming moistened cloth towels in a container comprising;
   (a) an insulating outer walls chamber having at least three outer walls defining a recess and wherein at least one of the outer walls defines a notch;
   (b) a heating means within said insulating walls and anchored to one of the walls;
   (c) an adapter with sufficient volume to hold a container having a projection along the adapter of like shape to the recess to fit within and contact the recess.

14. The cloth warmer of claim 13 wherein the adapter defines a slot.

15. A cloth warmer warming moistened cloth towels in a container with a lip comprising;
   (a) an insulating outer chamber having at least 3 walls and a floor defining a recess of like circumference to receive the lip of the container and having an area defined by the circumference along the inner surface of the recess which is less than the area defined by the circumference of the walls where they contact the floor;
   (b) a heating means within said outer walls and attached to one of said outer walls.

* * * * *